United States Patent [19]

Mirzadeh et al.

[11] Patent Number: 5,774,782
[45] Date of Patent: Jun. 30, 1998

[54] TECHNETIUM-99M GENERATOR SYSTEM

[75] Inventors: Saed Mirzadeh, Knoxville; Furn F. Knapp, Jr., Oak Ridge; Emory D. Collins, Knoxville, all of Tenn.

[73] Assignee: Lockheed Martin Energy Systems, Inc., Oak Ridge, Tenn.

[21] Appl. No.: 619,376

[22] Filed: May 22, 1996

[51] Int. Cl.$^6$ .................................................. C01G 57/00
[52] U.S. Cl. ...................... 423/2; 210/682; 250/432 PD; 424/1.65
[58] Field of Search .................. 423/2, 249; 210/682; 250/432 PD; 376/189; 424/1.65

[56] References Cited

U.S. PATENT DOCUMENTS

| | | | |
|---|---|---|---|
| 4,001,387 | 1/1977 | Barak et al. | 424/1 |
| 4,176,158 | 11/1979 | Laidler et al. | 423/2 |
| 4,272,503 | 6/1981 | Camin et al. | 424/1 |
| 4,738,834 | 4/1988 | Moore et al. | 423/2 |
| 5,186,913 | 2/1993 | Knapp et al. | 423/2 |
| 5,275,802 | 1/1994 | Knapp et al. | 424/129 |
| 5,604,264 | 2/1997 | McQuigg | 521/38 |

OTHER PUBLICATIONS

S. Seifert, G. Wagner and A. Eckardt, "Highly Concentrated [$^{99m}$Tc] Pertechnetate Solutions from (n,v)$^{99}$Mo/$^{99m}$Tc Generators for Nuclear Medicine Use", *Appl. Radiat. Isot.*, 45, 577 (1994).

N. C. Schroeder, "Technetium Partitioning for Hanford Tank Waste Remediation System: Sorption of Tehcnetium from DSS and DSSF–7 Waste Stimulants Using Rellex–HPQ Resin", LAUR–95–40, Jan. 6, 1995.

*Primary Examiner*—Ngoclan Mai
*Attorney, Agent, or Firm*—Joseph A. Marasco

[57] ABSTRACT

A $^{99}$Mo/$^{99m}$Tc generator system includes a sorbent column loaded with a composition containing $^{99}$Mo. The sorbent column has an effluent end in fluid communication with an anion-exchange column for concentrating $^{99m}$Tc eluted from the sorbent column.

A method of preparing a concentrated solution of $^{99m}$Tc includes the general steps of:

a. providing a sorbent column loaded with a composition containing $^{99}$Mo, the sorbent column having an effluent end in fluid communication with an anion-exchange column;

b. eluting the sorbent column with a salt solution to elute $^{99m}$Tc from the sorbent and to trap and concentrate the eluted $^{99m}$Tc on the ion-exchange column; and c. eluting the concentrated $^{99m}$Tc from the ion-exchange column with a solution comprising a reductive complexing agent.

4 Claims, 1 Drawing Sheet

TECHNETIUM-99M GENERATOR SYSTEM

The United States Government has rights in this invention pursuant to Contract No. DEAC05-84OR21400 between the United States Department of Energy and Lockheed Martin Energy Systems, Inc.

FIELD OF THE INVENTfON

The present invention relates to processes for the production of technetium-99m ($^{99m}$Tc) via decay of molybdenum-99 ($^{99}$Mo), and more particularly to such processes which involve utilization of $^{99}$Mo produced via neutron capture of a $^{98}$Mo target.

BACKGROUND OF THE INVENIION $^{99m}$Tc is the principal radioisotope used in diagnostic nuclear medicine with an estimated 10million medical tests per year and $34 billion cost to patients annually. This radioisotope is produced from the decay of $^{99}$Mo which at the present time is produced from fission of uranium-235 ($^{235}$U) and is primarily available from Nordion Inc., Canada.

For the following three reasons there are distinct long-term advantages for the routine production of $^{99}$Mo via alterative routes.

1. The fission route produces very high levels of radioactive waste including several radioactive gases, thus requiring complex, dedicated processing and waste disposal facilities which are nearly prohibitively expensive to operate.

2. In the fission produced $^{99}$Mo, the target material is highly enriched $^{235}$U which is a weapons grade substance requiring extensive safeguards. As a part of the international nuclear non-proliferation movement led by United States, there is concern about availability of highly enriched $^{235}$U in the near future.

3. There are environmental issues which are an integral part of such processes. During chemical processing of irradiated $^{235}$U, there exists potential for catastrophic criticality accidents resulting in release of highly radioactive fission products.

Concerning the manufacture and use of $^{99}$Mo/$^{99m}$Tc generators, the principal issue which differentiates fission produced $^{99}$Mo (Mo-F) from direct neutron capture produced $^{99}$Mo (Mo-N) is specific activity. The theoretical specific activity of Mo-F is 480 Ci/mg. Commercially available $^{99}$Mo/$^{99m}$Tc generators require $^{99}$Mo having specific activity of 1–2 Ci/mg. Fission-produced $^{99}$Mo has specific activity of about 100 Ci/mg, whereas specific activity of neutron capture produced $^{99}$Mo, even that produced in the highest available neutron flux (the well known hydraulic tube facility of the High Flux Isotope Reactor located at the Oak Ridge National Laboratory, Oak Ridge, Tenn.), is in order of 50–100 mCi/mg—a factor of up to 40 times lower than required for conventional generator systems. For example, in one widely used generator, $^{99}$Mo is loaded onto a column of alumina and $^{99m}$Tc is eluted from the column with normal saline. The required bolus volume for the quantitative elution of $^{99m}$Tc obviously depends on the size of the column which in turn is inversely proportional to the specific activity of $^{99}$Mo. Thus the lower specific activity of neutron-capture-produced $^{99}$Mo requires a larger alumina column, and hence the specific volume of $^{99m}$Tc (mCi /mL) is lower.

In order to provide $^{99m}$Tc in the specific volumes which are attainable from a fission-produced $^{99}$Mo/$^{99m}$Tc generator, methods of concentrating $^{99m}$Tc have been suggested by S. Seifert, G. Wagner and A. Eckardt, "Highly Concentrated [$^{99m}$Tc] Pertechnetate Solutions from (n,γ) $^{99}$Mo/$^{99m}$Tc Generators for Nuclear Medicine Use", Appl Radiat. Isot., 45, 577 (1994). Such an approach for concentration of $^{99m}$Tc is a two-step, rather complex process which is not readily amenable to automation. For example, in that method, $^{99m}$Tc is first eluted from an alumina column with normal saline, followed by reduction of the pertechnetate by addition of SnCl$_2$. The reduced $^{99m}$Tc is then loaded on a second alumina column and is then oxidized by washing the column with a solution of ammonium hydroxide containing H$_2$O$_2$. After evaporating the H$_2$O$_2$ at elevated temperature, $^{99m}$Tc is eluted with 2-3 mL of normal saline from the second alumina column. It is thus evident that a need exists for an inherently simple method which can be easily operated.

A two-stage tandem generator system was developed for concentration of carrier-free $^{188}$Re. See U.S. Pat. No. 5,186,913, issued Feb. 16, 1993 and U.S. Pat. No. 5,275,802, issued Jan. 4, 1994, both issued to F. F. Knapp, E. C. Lisic, S. Mirzadeh, and A. P. Callahan, and entitled, "Tungsten-188/Carrier free Re-188 Perrhenic Acid Generator System". In part of the process taught therein, "$^8$Re is eluted from an anion-exchange column with strong HNO$_3$, followed by evaporation of HNO$_3$ to near dryness for conversion of $^{188}$Re to the chloride form. The conversion step is not amenable to simple operation.

N. C. Schroeder, "Technetium Partitioning for Hanford Tank Waste Remediation System: Sorption of Technetium from DSS and DSSF-7 Waste Stimulants Using Rellex-HPQ Resin", LAUR-95-40, Jan. 6, 1995, primarily deals with the separation of long-lived $^{99}$Tc from legacy waste. $^{99}$Tc is adsorbed onto an anion exchange resin followed by reductive elution of $^{99}$Tc with a solution containing a complexing agent, ethylenediamine (EDA).

There is a need to provide a method of reconcentrating $^{99m}$Tc produced by decay of $^{99}$Mo, thus providing an inherently simple method and a device that can be easily operated.

It should be understood that when isotopes are referred to herein by a simple term such as $^{99}$Tc, that a solution containing that isotope is usually what is inferred.

OBJECTS OF THE INVENTION

Accordingly, it is an object of the present invention to provide new and improved processes for the production of $^{99m}$Tc which do not involve the use of $^{235}$U.

It is another object of the present invention to provide new and improved processes for the production of $^{99m}$Tc which do not involve nuclear fission of $^{235}$U.

It is also an object of the present invention to provide new and improved processes for the production of $^{99m}$Tc which do not produce large amounts of radioactive waste.

It is a further object of the present invention to provide new and improved processes for the production of $^{99m}$Tc which involve the production of $^{99}$Mo via a non-fission process.

It is yet another object of the present invention to provide new and improved processes for the production of $^{99m}$Tc which minimize health and environmental risks.

It is yet a further object of the present invention to provide new and improved processes for the production of $^{99m}$Tc which significantly increase availability thereof, while significantly reducing unit cost thereof It is another object of the present invention to provide a method of reconcentrating $^{99m}$Tc produced by decay of $^{99}$Mo.

It is another object of the present invention to provide $^{99m}$Tc in highly concentrated form.

It is another object of the present invention to provide $^{99m}$Tc produced by a non-fission route in specific volume (mCi/mL) comparable to that obtainable from the fission route.

It is a further object of the present invention to provide $^{99m}$Tc which is suitable for subsequent radiopharmaceutical formulations, such as attachments of $^{99m}$Tc to antibodies.

Further and other objects of the present invention will become apparent from the description contained herein.

SUMMARY OF THE INVENION

In accordance with one aspect of the present invention, the foregoing and other objects are achieved by a method of preparing a concentrated solution of $^{99m}$Tc includes the general steps of:

a. providing a sorbent column loaded with a composition containing $^{99}$Mo, the sorbent column having an effluent end in fluid communication with an anion-exchange column;

b. eluting the sorbent column with a salt solution to elute $^{99m}$Tc from the sorbent and to trap and concentrate the eluted $^{99m}$Tc on the ion-exchange column; and c. eluting the concentrated $^{99m}$Tc from the ion-exchange column with a solution comprising a reductive complexing agent.

Figure 1:
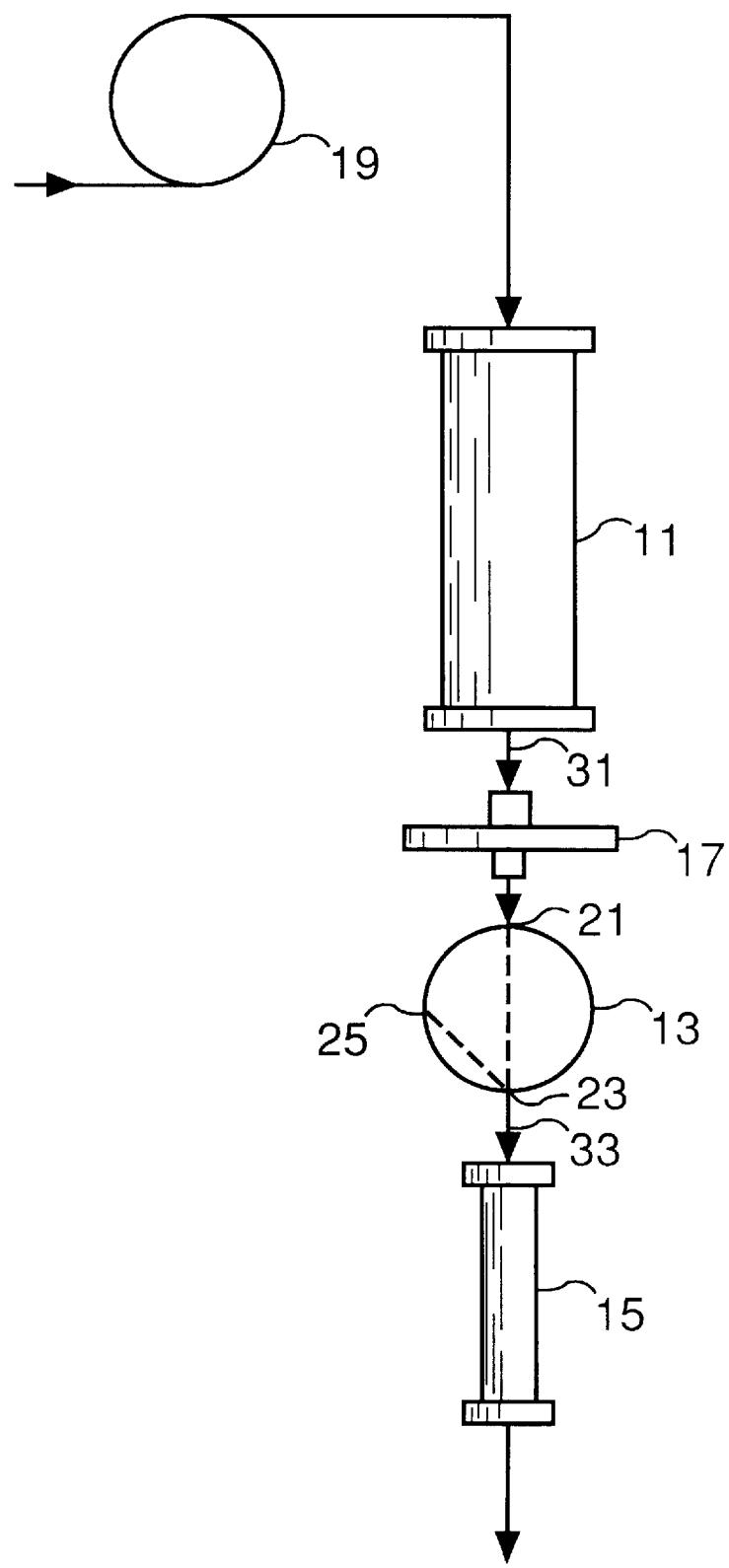
FIG. 1 is an apparatus suitable for use in carrying out the present invention.

For a better understanding of the present invention, together with other and further objects, advantages and capabilities thereof, reference is made to the following disclosure and appended claims in connection with the above-described drawings.

DETAILED DESCRIPTION OF THE INVENTION

Development of Preferred Method

On the basis of our experience with the development of the two-stage tandem generator system for preparation of carrier-free $^{188}$Re, we expected that carrier-free $^{99m}$Tc (which chemically resembles Re) should be strongly retained in a small anion exchange column from a dilute solution of NH$_4$NO$_3$ and then eluted with strong HNO$_3$. In a typical study, $^{99m}$Tc was eluted from a $^{99}$Mo-N generator with 10 mL of 0.1 M NH$_4$NO$_3$ and loaded onto an anion exchange column (2×10 mm, Dowex AG W 1X8, 100–200 mesh, N0$_3$- form preequilibrated with the 0.1 M NH$_4$NO$_3$). The column was then washed with 5 mL of 0.1 M NH$_4$NO$_3$ and followed by 2 mL of H$_2$O. Subsequently, $^{99m}$Tc was quantitatively stripped from the column with 3×1 mL of 6 M HNO$_3$. Because of high volatility, solutions of $^{99m}$Tc in nitric acid were deemed impractical for use in a hospital setting. Thus, another method was needed for quantitative elution of $^{99m}$Tc from the anion-exchange column.

Subsequently, it was found that the retained $^{99m}$Tc on such an anion-exchange column can be eluted with a weakly basic solution of stannous chloride (SnCl$_2$) and ethylenediamine (EDA). Such a column is herein after referred to as a $^{99m}$Tc concentrator column.

The following steps set forth a suitable method of carrying out the invention. It should be understood that parameters such as molarities, amounts, etc. are expressed as generalities and are not to be construed as critical to the operability of the invention.

Step 1. A typical sorbent (usually adsorbent) type generator column is charged with an adsorbent such as alumina, zirconia, zirconium molybdate, etc. and pre-equilibrated, usually with a salt solution such as 0.1 M NH$_4$NO$_3$.

Step 2. Molybdenum is loaded on the column as $MoO_4^{2-}$ or hydrated MoO$_3$ at pH 3–4. The loading solution can be prepared, for example, by titrating about 1 mL of a 0.003 mg/L $^{99}$Mo stock solution (~3 mg) with 1 M HNO$_3$.

Step 3. $^{99m}$Tc is eluted from a $^{99}$Mo-N alumina generator with a salt solution such as 0.1 M NH$_4$NO$_3$ or normal saline.

Step 4. The eluted solution is loaded onto a $^{99m}$Tc concentrator column containing, for example 2×10 mm, Dowex AG W 1X8, 100–200 mesh, NO$_3$- form preequilibrated with 0.1 M NH$_4$NO$_3$. Most commercially available anion exchange resins are suitable for this step, for example, Dowex AG 1, Dowex AG 2, Dowex AG 4, REILLEX HPQ, REILLEX 402, etc.

Step 5. The $^{99m}$Tc concentrator column is washed with a small amount of 0.1 M NH$_4$NO$_3$ followed by a small amount of H$_2$O.

Step 6. $^{99m}$Tc is stripped from the column with 5 small portions of a reductive complexing agent such as EDA reagent, which is a mixture comprising, for example, about 0.004 parts of SnCl$_2$ about 1 part of 10% EDA/H$_2$O, about 1 part of 0.1 M NaOH and about 10 parts of H$_2$O, purged with N$_2$). Other suitable complexing agents include, but are not limited to molecules containing at least one of these functional groups: amines, amides, ketones, organic acids, organic bases, dithiol chelating groups.

Many salt solutions are suitable for use instead of the preferred 0.1 M NH$_4$NO$_3$ described above. Other examples include solutions of NaNO$_3$, NH$_4$Cl, NaCl, etc.

Description of Preferred Generator System

A suitable generator system is shown schematically in FIG. 1, with arrows showing the flow of fluid into and out of system components. An alumina column 11, generally having a capacity of about 25–1000 mL, is attached via a three-way valve 13 to a smaller $^{99m}$Tc concentrator column 15, which generally has a capacity of about 1–5 mL. A submicron filter (for example, 0.22 μm) 17 is preferably located at the exit end of the alumina column for preventing adsorbent particles from contaminating the $^{99m}$Tc concentrator column 15. A peristaltic or other type of pump 19 can be used to force fluid through the system.

In a preferred configuration, a first port 21 of the three-way valve 13 is attached to the effluent 31 of the alumina generator 11, and a common port 23 of the three-way valve 13 is attached to the inlet 33 of the $^{99m}$Tc concentrator column 15. A second port 25 of the three-way valve 13 is used to introduce fluids directly into the $^{99m}$Tc concentrator column 15 in order to perform functions such as elution of purified $^{99m}$Tc solutions therefrom and regeneration and washing thereof.

The function of the three-way valve 13 can be achieved by a simple Y-connection, with backflow preventing means such as pinchcocks or check valves in the influent lines (not illustrated). Check valves would not require attention such as that needed to operate pinchcocks or a three-way valve. It is also evident to those skilled in the art that there are other possible configurations of various conventional components that are suitable for carrying out the present invention. The invention is not limited by the apparatus used to carry out the method.

Operation of Preferred Generator System

The following is a more specific description of a preferred embodiment of the present invention, to include how to carry out a preferred embodiment of the invention via the preferred generator system.

Prior to elution of $^{99m}$Tc from the generator system, the three-way valve 13 is adjusted so that the second port 25 communicates with the common port 23. Through the second port 25, the $^{99m}$Tc concentrator column 15 is preferably equilibrated, for example, with about 5 mL of 0.1 M NH$_4$NO$_3$.

The $^{99m}$Tc concentrator column 15 is preferably regenerated after each use thereof. For example, regeneration can be carried out by the following sequence: about 5 mL each of 0.1 M NaOH, H$_2$O, 0.1 M HNO$_3$, H$_2$O, through the second port 25.

The three-way valve is adjusted so that the first port 21 communicates with the common port 23. The generator system is cluted with about 10 mL of 0.1 M NH$_4$NO$_3$ or normal saline. The eluted $^{99m}$Tc is trapped and concentrated in the $^{99m}$Tc concentrator column 15.

The three-way valve 13 is adjusted so that the second port 25 communicates with the common port 23. The $^{99m}$Tc concentrator column 15 is washed, through the second port 25, with about 2 mL of each 0.1 M NH$_4$NO$_3$ and H$_2$O, The $^{99m}$Tc is then cluted with 5 portions of about 0.5 mL of the EDA reagent to obtain about a ten-fold concentration thereof.

The method can be succesfully repeated using a single $^{99}$Mo-N charge 5 times or more, extended over 2 weeks (shelf-life of $^{99}$Mo-N).

EXAMPLE I $^{99m}$Tc was eluted from a $^{99}$Mo-N alumina generator with 10 mL of 0.1 M NH$_4$NO$_3$. The eluted solution was loaded onto a $^{99m}$Tc concentrator column (2×10 mm, Dowex AG W 1X8, 100–200 mesh, NO$_3$ form preequilibrated with the 0.1 M NH$_4$NO$_3$). After loadin& the column was washed with 2 mL of 0.1 M NH$_4$NO$_3$ followed by 2 mL of H$_2$O. Subsequenty, $^{99m}$Tc was stripped from the column with 5×0.5 mL of EDA reagent (a freshly prepared mixture of 4.0 mg of SnCl$_2$, 1 mL of 10% EDA/H$_2$O, 1.0 mL of 0.1 M NaOH and 10 mL of H$_2$O, purged with N$_2$). As shown in Table 1, greater than 75% of $^{99m}$Tc is eluted in the first two-4.5 mL portions of EDA reagenL The specific volume of $^{99m}$Tc was 0.35 mCi/mL after elution from alumina column, and 2.7 mCi/imL after concentration—a factor of 8 increase in concentration thereof.

TABLE 1

Typical data from operation of $^{99}$Mo/$^{99m}$Tc generator system

| Step | Time | Operation step/Sample | $^{99m}$Tc activity mCi | % |
|---|---|---|---|---|
| 1 | 10:05 | Elution of $^{99m}$Tc from alumina column (10 mL, 0.9% NaCl) | 3.50 | 100 |
| 2 | 10:12 | $^{99m}$Tc concentrator column load | 0.350 | 10 |
|   |   | wash 1, (2 mL, 0.1 M NH$_4$NO$_3$) | 0.010 | 0.03 |
|   |   | wasb 2, (2 mL, H$_2$O) | 0.006 | 0.020 |
| 3 | 10:22 | Strip 1, (0.5 mL of EDA reagent) | 2.10 | 60.0 |
|   | 10:28 | Strip 2, (0.5 mL of EDA reagent) | 0.60 | 17.1 |
|   | 10.30 | Strip 3, (0.5 mL of EDA reagent) | 0.126 | 3.6 |
|   | 10.32 | Strip 4, (0.5 mL of EDA reagent) | 0.036 | 1.0 |
|   | 10:34 | Strip 5, (0.5 mL of EDA reagent) | 0.104 | 3.0 |
| Total steps 2 & 3 |   |   | 3.33 | 95.1 |

Moreover, upon acidification of the $^{99m}$Tc-EDA complex to a pH of about 4, the EDA ligand readily exchanges with other ligands such as citrate or gluconate with 92–94% complexation within 30 minutes (citrates and gluconates are typical ligands used in the process of $^{99m}$Tc labeling of various tissue specific agents).

EXAMPLE II $^{99m}$Tc-EDA complex prepared in accordance with Example I was acidified to a pH of about 4 by addition of 500 μL 0.5 of M citrate buffer (pH=4.2). The EDA ligand exchanged with the citrate ligand, with 92–94% complexation within 30 minutes.

EXAMPLE III $^{99m}$Tc-EDA complex prepared in accordance with Example I was acidified to a pH of about 4 by addition of 500 μL 0.5 of M gluconate buffer (pH=4.2). The EDA ligand exchanged the gluconate ligand, with 92–94% complexation within 30 minutes.

Furthermore, the $^{99m}$Tc-gluconate complex prepared via exchange with EDA can be used for direct labeling of an antibody with $^{99m}$Tc with yields of greater than 80% within one hour.

EXAMPLE IV $^{99m}$Tc-gluconate complex prepared in accordance with Example III was used for direct labeling of an antibody with $^{99m}$Tc with yields of greater than 80% within one hour.

Unique advantages of this invention include:

1. The neutron capture route utilized in the preferred embodiment of the present invention generates minimal waste and does not require a dedicated processing facility. The fission route, on the other hand, produces very high levels of radioactive waste including several radioactive gases, thus requiring dedicated processing facilities which are expensive to operate.

2. The target material for production of $^{99m}$Tc by the neutron capture route is enriched $^{98}$Mo. This eliminates the necessity for the use of highly enriched $^{235}$U (the current target material) which is a weapons grade substance requiring extensive safeguards.

3. Enriched $^{98}$Mo is readily available, whereas availability of highly enriched $^{235}$U in near future is in doubt.

4. In relative terms, the neutron capture route is by far more environmentally friendly than the fission route, where the potential for a catastrophic accident exists resulting in release of fission products.

Moreover, the invention is useful for concentrating $^{99m}$Tc product of fission-produced Mo-F. The useful shelf-life of Mo-F/$^{99m}$Tc generator is about a week. After this period, the specific volume (mCi/mL) of $^{99m}$Tc becomes too low for mrrost clinical use. The above described $^{99m}$Tc concentrator is also suitable for use with fission Mo generator, therefore by attaching the $^{99m}$Tc concentrator to the outlet of a conventional Mo-F/$^{99m}$Tc generator, the shelf-life of such generators can be substantially extended.

While there has been shown and described what are at present considered the preferred embodiments of the invention, it will be obvious to those skilled in the art that various changes and modifications can be made therein without departing from the scope of the inventions defined by the appended claims.

What is claimed is:

1. A method of preparing a concentrated solution of $^{99m}$Tc comprising the steps of:
   a. providing a sorbent column loaded with a composition containing $^{99}$Mo, said sorbent column having an effluent end in fluid communication with an anion-exchange column;

b. eluting said sorbent column with a salt solution to elute a first eluate comprising $^{99m}$Tc from said sorbent and to-trap said eluted $^{99m}$Tc on said ion-exchange column;

c. eluting said $^{99m}$Tc from said ion-exchange column with a solution comprising a reductive complexing agent to elute a second eluate comprising said $^{99m}$Tc in the form of complexed. reduced $^{99m}$Tc in a concentration at least 8 times greater than the concentration of said $^{99m}$Tc in said first eluate: and, d. acidifying said complexed. reduced $^{99m}$Tc to produce a $^{99m}$Tc product in a form which is suitable for subsequent radiopharmaceutical use.

2. A method of preparing a concentrated solution of $^{99m}$Tc in accordance with claim 1 wherein said sorbent comprises at least one of alumina, zirconia, or zirconium molybdate.

3. A method of preparing a concentrated solution of $^{99m}$Tc in accordance with claim 1 wherein said anion-exchange column contains an anion exchange resin comprising at least one of Dowex AG W 1X8, Dowex AG 1, Dowex AG 2, Dowex AG 4, REILLEX HPQ, or REILLEX 402.

4. A method of preparing a concentrated solution of $^{99m}$Tc in accordance with claim 1 wherein said reductive complexing agent comprises EDA.

* * * * *